United States Patent
Guo

(10) Patent No.: US 11,266,131 B2
(45) Date of Patent: Mar. 8, 2022

(54) MOLLUSCAN SHELLFISH PRODUCED BY CONTROLLED CROSSBREEDING

(71) Applicant: Rutgers, The State University of New Jersey, New Brunswick, NJ (US)

(72) Inventor: Ximing Guo, Sewell, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 264 days.

(21) Appl. No.: 16/352,049

(22) Filed: Mar. 13, 2019

(65) Prior Publication Data

US 2019/0281800 A1 Sep. 19, 2019

Related U.S. Application Data

(60) Provisional application No. 62/642,892, filed on Mar. 14, 2018.

(51) Int. Cl.
*A01K 67/033* (2006.01)
*A01K 61/54* (2017.01)

(52) U.S. Cl.
CPC .......... *A01K 67/0334* (2013.01); *A01K 61/54* (2017.01)

(58) Field of Classification Search
CPC ............................ A01K 67/0334; A01K 61/54
See application file for complete search history.

(56) References Cited

U.S. PATENT DOCUMENTS 5,824,841 A 10/1998 Guo et al. .......... 800/2

FOREIGN PATENT DOCUMENTS

FR 2913983 3/2007

OTHER PUBLICATIONS

De Sousa (2016, Genome, 59:327-338).*
Degremont (2012, Journal of Shellfish, 31:21-31).*
Calvo et al. "Dual disease resistance in a selectively bred eastern oyster, *Crassostrea virginica*, strain tested in Chesapeake Bay" Aquaculture 2003 220(1-4):69-87.
Evans et al. "The effects of inbreeding on performance traits of adult Pacific oysters (*Crassostrea gigas*)" Aquaculture 2004 230(1-4):89-98.
Ford, S.E. and Haskin, H.H. "Infection and mortality patterns in strains of oysters *Crassostrea virginica* selected for resistance to the parasite Haplosporidium nelsoni (MSX)" Journal.
Gregory, K.E. and Cundiff, L.V. "Crossbreeding in Beef Cattle: Evaluation of Systems" Journal of Animal Science 1980 51(5):1224-1242.
Guo et al. Chromosome set manipulation in shellfish. pp. 165-195 in: New Technologies in Aquaculture: Improving Production Efficiency, Quality and Environmental management, G. Burnell and G. Allan (eds). Woodhead Publishing 2009.
Guo et al. "Building a Superior Oyster for Aquaculture" the Jersey Shoreline 2008 25(1):7-9.
Guo et al. "All-triploid Pacific Oysters (*Crassostrea gigas* Thunberg) produced by mating tetraploids and diploids" Aquaculture 1996 142:149-161.
Guo et al. "Breeding and evaluation of eastern oyster strains selected for MSX, DERMO and JOD resistance" J. Shellfish Res. 2003 22(1):333-334.
Guo, X. and Allen, S.K. "Viable tetraploids in the Pacific oyster (*Crassostrea gigas* Thunberg) produced by inhibiting polar body 1 in eggs from triploids" Mol. Mar. Biol. Biotech. 1994 3(1):42-50.
Hedgecock et al. "Hybrid vigor in Pacific oysters: an experimental approach using crosses among inbred lines" Aquaculture 1995 137(1-4): 285-298.
Johnson, R.K. "Crossbreeding in swine: experimental results" Journal of Animal Science, 1981 52(4):906-923.
Langdon et al. "Yields of cultured Pacific oysters *Crassostrea gigas* Thunberg improved after one generation of selection" Aquaculture 2003 220(1-4):227-244.
Launey, S. and Hedgecock, D. "High genetic load in the Pacific oyster *Crassostrea gigas*" Genetics 2001 159(1):255-265.
Lionel et al. "Genetic improvement for disease resistance in oysters: A review" Journal of invertebrate pathology 2015 131:226-241.
McCombie et al. "A complementary method for production of tetraploid *Crassostrea gigas* using crosses between diploids and tetraploids with cytochalasin b treatments" Marine Biotechnology 2005 7(4):318-330.
Ward et al. "Genetic Improvement of the Pacific oyster *Crassostrea gigas* (Thunberg) in Australia" Aquaculture Research 2000 31(1):35-44.
Z. and Guo, X. "Genetic linkage map of the eastern oyster *Crassostrea virginica* Gmelin" Biol. Bull. 2003 204: 327-338.

* cited by examiner

*Primary Examiner* — Valarie E Bertoglio
(74) *Attorney, Agent, or Firm* — Licata & Tyrrell P.C.

(57) ABSTRACT

Improved molluscan shellfish in diploid, tetraploid and triploid forms are provided. Also provided are methods for improving molluscan shellfish through progressive rotational crossbreeding and/or coalesced interploidy breeding.

6 Claims, 2 Drawing Sheets

MOLLUSCAN SHELLFISH PRODUCED BY CONTROLLED CROSSBREEDING

INTRODUCTION

This patent application claims the benefit of priority from U.S. Provisional Application Ser. No. 62/642,892, filed Mar. 14, 2018, teachings of which are herein incorporated by reference in their entirety.

This invention was made with government support under grant number 2015-70007-24245 awarded by the United States Department of Agriculture National Institute of Food and Agriculture. The government has certain rights in the invention.

FIELD OF THE INVENTION

The present invention relates to methods for the improvement of molluscan shellfish in diploid, tetraploid and triploid forms as well as improved molluscan shellfish in diploid, tetraploid and triploid forms.

BACKGROUND

Molluscan shellfish are important aquaculture species. They support significant aquaculture industries worldwide. Major molluscan aquaculture species include oysters, clams, scallops, mussels and abalone. Unlike livestock that have a long history of domestication, molluscan species are mostly wild and lack characteristics desired for aquaculture production.

Molluscan stocks can be improved through selective breeding and ploidy manipulation (Ward et al. Aquaculture Research 2000 31(1):35-44; Guo et al. Chromosome set manipulation in shellfish. Pp 165-195 in: New Technologies in Aquaculture: Improving Production Efficiency, Quality and Environmental management, G. Burnell and G. Allan (eds). Woodhead Publishing 2009; and Degremont et al. Journal of invertebrate pathology 2015 131:226-241). Selective breeding of cultured mollusks have been done through individual or family-based selection. For example, individual selection in the eastern oyster Crassostrea virginica has produced strains that show strong resistance to diseases (Ford and Haskin Journal of Parasitology 1987 73:268-376; Calvo et al. Aquaculture 2003 220(1-4):69-87; Guo et al. J. Shellfish Res. 2003 22(1):333-334). Family-based selection has been used to improve yield in the Pacific oyster Crassostrea gigas (Langdon et al. Aquaculture 2003 220(1-4): 227-244).

Crossbreeding between pure lines, which is widely used for genetic improvement of livestock (Gregory and Cundiff, Journal of Animal Science 1980 51(5):1224-1242; Johnson, R. K. Journal of Animal Science, 1981 52(4):906-923), has not been successfully applied to molluscan breeding. It has been shown in oysters that crossbreeding between inbred lines can produce hybrid vigor and is potentially useful for oyster breeding (Hedgecock et al. Aquaculture 1995 137(1-4): 285-298; Guo et al. The Jersey Shoreline 2008 25(1):7-9). Practical application of this approach in molluscan breeding has been limited by a lack of pure or inbred lines. Inbred lines are easy to produce but difficult to maintain in mollusks. Mollusks are mostly wild with no or little history of domestication. They are highly polymorphic and contain high levels of recessive lethal genes (Launey and Hedgecock Genetics 2001 159(1):255-265; Yu and Guo Biol. Bull. 2003 204: 327-338). As such, rapid inbreeding in mollusks often leads to severe inbreeding depression (Evans et al. Aquaculture 2004 230(1-4):89-98). Inbred lines often fail within a few generations of closed breeding. Thus, traditional rotational crossing of pure lines used in livestock breeding cannot be easily applied to molluscan breeding.

Molluscan shellfish can also be improved by ploidy manipulation or through the production of triploids (3N) that contain three sets of chromosomes (Guo et al. Chromosome set manipulation in shellfish. Pp 165-195 in: New Technologies in Aquaculture: Improving Production Efficiency, Quality and Environmental management, G. Burnell and G. Allan (eds). Woodhead Publishing 2009). Because of the extra set of chromosomes, triploid mollusks exhibit several characteristics desired for aquaculture. Triploids are mostly sterile, grow fast and maintain high-quality meat throughout the year. Triploid oysters have become an important part of the oyster aquaculture industry. As triploids are mostly sterile, they cannot be reproduced or directly improved by selective breeding. Triploid mollusks are produced by crossing diploids and tetraploids (4N) that contain four sets of chromosomes (Guo et al. Aquaculture 1996 142:149-161). Thus, triploids can only be improved by improving their diploid and tetraploid parents.

The first generation of tetraploids is produced by inhibiting polar body I in eggs from triploids fertilized with sperm from diploids (U.S. Pat. No: 5,824,841; Guo and Allen Mol. Mar. Biol. Biotech. 1994 3(1):42-50). Because tetraploids are fertile, tetraploids can be reproduced by 4N×4N crosses, which is how tetraploids are currently produced and bred. While breeding tetraploids through 4N×4N crosses is easy, it can lead to inbreeding of tetraploids. Two methods are available for introducing new genetic material from diploids either by inhibiting polar body II in 2N×4N crosses (McCombie et al. Marine Biotechnology 2005 7(4):318-330; FR Patent No. 2913983-A1) or by inhibiting polar body I in 2N×2N crosses (FR Patent No. 2913983-A1). These methods bypass triploids and therefore cannot bring in any improvement made in triploids into the tetraploid line. Genes that are particularly good for triploids are not transmitted to tetraploids that are used for the production of triploids. The disconnect between the tetraploid and triploid phases means that selection in tetraploids may not lead to genetic improvement of triploids, which is the actual stock used for production.

New methods for improving cultured mollusks are needed to support aquaculture development.

SUMMARY

An aspect of the present invention relates to methods for the improvement of molluscan shellfish in diploid, tetraploid and triploid forms.

In one nonlimiting embodiment, a method is provided for breeding a diploid mollusk with improved performance in aquaculture production through progressive rotational crossbreeding. The method comprises deriving multiple semi-inbred core lines of diploid mollusks from independent source populations of diploid mollusks which are progressively improved through strong individual selection. The method further comprises preventing severe inbreeding or complete loss of the multiple semi-inbred core lines through a bridging line that is produced by progressive crossing and backcrossing between the core line and the source population and strong individual selection. The method further comprises rotating the multiple semi-inbred core lines for crossing with the production line so that genetic diversity and heterosis in the production line are sustained.

In another nonlimiting embodiment, a method is provided for producing tetraploid mollusks with improved performance in aquaculture production through coalesced interploidy breeding. The method comprises systematically integrating selection across diploid, triploid and tetraploid phases. In one nonlimiting embodiment, the method comprises producing mated tetraploids by tetraploid×tetraploid crosses and subjecting the mated tetraploids to strong individual selection. In another nonlimiting embodiment, triploids are produced by crossing tetraploids and diploids to bring in one new set of chromosomes into triploids followed by subjecting the triploids to strong individual selection. In yet another nonlimiting embodiment, de novo tetraploids are produced by mating selected triploids and selected diploids followed by polar body I inhibition and subjecting the produced tetraploids to strong individual selection. In this nonlimiting embodiment, the de novo tetraploids can be crossed with mated tetraploids to produce improved tetraploids that contain increased genetic diversity and favorable genes selected from the diploid, triploid and tetraploid phases.

Another aspect of the present invention relates to methods for producing triploid mollusks. In one nonlimiting embodiment, the triploid mollusks are produced via crossing of any tetraploid mollusk with a diploid mollusk produced in accordance with progressive rotational crossbreeding as disclosed herein. In another nonlimiting embodiment, the triploid mollusk is produced via crossing of any diploid mollusk with a tetraploid mollusk produced in accordance with coalesced interploidy breeding as disclosed herein. In yet another nonlimiting embodiment, the triploid mollusks are produced via crossing of a diploid mollusk produced in accordance with progressive rotational crossbreeding as disclosed herein and a tetraploid mollusk produced in accordance with coalesced interploidy breeding as disclosed herein.

Yet another aspect of the present invention relates to improved molluscan shellfish in diploid, tetraploid and triploid forms.

In one nonlimiting embodiment, the mollusk is an oyster.

DETAILED DESCRIPTION

Figure 1:
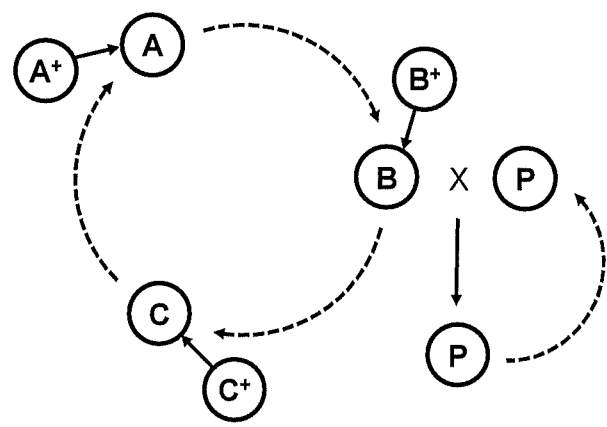
FIG. 1 provides a diagram of a nonlimiting embodiment of progressive rotational crossing (PRC) used in the present invention where each of the core lines (A, B, and C) are derived from a different population, progressively improved by strong selection and rotated for crossing with the production line (P). To prevent severe inbreeding and complete failure, each core line is supported with a more heterozygous bridging line that is produced by progressive crossing and backcrossing between the core line and the source population.

Disclosed herein are methods for the improvement of molluscan shellfish in diploid, tetraploid and triploid forms and molluscan shellfish improved in accordance with these methods. Methods for crossbreeding mollusks of the present invention do not rely on the use of pure or inbred lines. Instead the methods and mollusks of the present invention exhibiting improved performance in aquaculture production are produced via progressive rotational crossbreeding and/or coalesced interploidy breeding. In one nonlimiting embodiment, the mollusk is an oyster.

The present invention provides a method for breeding diploid mollusks with improved performance in aquaculture production through progressive rotational crossbreeding.

The method referred to herein as progressive rotational crossbreeding or PRC utilizes and sustains genetic diversity for progressive improvement of multiple core lines for rotational crossbreeding. By multiple, as used herein, it is meant 3 or more core lines. Genetic diversity is maintained through bridging lines that are producing through progressive crossing and backcrossing between the core lines and source populations. Progressive improvements are achieved by applying strong individual selection to both core and bridging lines. The rotational crossing retains genetic diversity and heterosis in the production line. The PRC process comprises a minimum of three independent core lines (A, B and C) and a production line (P) that are used for commercial production. In the nonlimiting embodiment depicted in FIG. 1, the three core lines are rotated for crossing with the production line to maintain genetic diversity and heterosis. The core lines are genetically independent and derived from different source populations or unrelated individuals from the same source population. In this nonlimiting embodiment, the core lines are progressively improved in each generation by applying strong individual selection by selecting, for example, the top 10% performers as parents. Each of the core lines is supported by a bridging line ($A^+$, $B^+$ or $C^+$) to maintain genetic diversity.

In one nonlimiting embodiment, the bridging lines are produced by progressive crossing and backcrossing between the core lines and their perspective source populations in the following steps: 1) F1s are produced by crossing the core line and a source population to bring in new genetic material; 2) F2s are produced by crossing F1s to expose homozygotes of both favorable and deleterious alleles to selection; and 3) F2s are backcrossed to the core line producing the backcross (BC) followed by a within-line (BC×BC) cross until the bridging line's performance is comparable to that of the core line. At each step of this nonlimiting embodiment, strong selection is applied by selecting, for example, the top 10% performers as parents. All crosses are factorial using at least 25 females and 25 males to maintain genetic diversity. Strong selection is balanced with the new genetic material from the bridging lines to prevent severe inbreeding and complete failure of the core lines.

Accordingly, in this method of the present invention for breeding diploid mollusks with improved performance in aquaculture production, multiple semi-inbred core lines of diploid mollusks are derived from independent source populations of diploid mollusks which are progressively improved through strong individual selection. The method further comprises preventing severe inbreeding or complete loss of the multiple semi-inbred core lines through a bridging line that is produced by progressive crossing and backcrossing between the core line and the source population and strong individual selection. The method further comprises rotating the multiple semi-inbred core lines for crossing with the production line so that genetic diversity and heterosis in the production line are sustained.

In contrast to traditional rotational crossing, the PRC process does not rely on the use of pure lines which are difficult to sustain in molluscan shellfish. Further, severe inbreeding or complete loss of the core lines is prevented through the use of bridging lines. In addition, both core lines and bridging lines are progressively improved by strong individual selection. Because the core lines are heterozygous or semi-inbred and genetically independent, the PRC method allows progressive improvement of the core lines through selection, while maintaining genetic diversity and heterosis. PRC can be used to establish core lines directly from wild populations and progressively improve them for rotational crossbreeding.

The present invention also provides methods for producing tetraploid mollusks with improved performance in aquaculture production through coalesced interploidy breeding.

Figure 2:
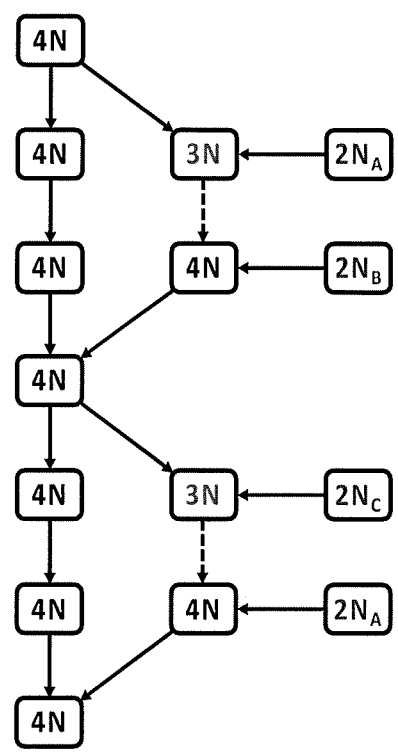
FIG. 2 provides a diagram of a nonlimiting embodiment of coalesced interploidy breeding (CIB) used in the present invention encompassing diploid (2N), triploid (3N) and tetraploid (4N) phases. The dash lines represent the production of de novo tetraploids by inhibiting polar body I in eggs of triploids fertilized by sperm from diploids. Each CIB cycle brings two sets of chromosomes from different diploid lines into de novo tetraploids through a triploid phase, where genes supporting superior triploids are enriched and brought into tetraploids.

The method referred to herein as coalesced interploidy breeding or CIB maintains genetic diversity through systematic integration of selective breeding across the diploid, triploid and tetraploid phases. CIB provides a mechanism where improvements in the diploid and triploid phases are systematically brought into the tetraploid lines for the production of improved triploids. In one nonlimiting embodiment, the method comprises producing mated tetraploids by tetraploid×tetraploid crosses and subjecting the mated tetraploids to strong individual selection. In another embodiment, triploids are produced by crossing tetraploids and diploids to bring in one new set of chromosomes into triploids followed by subjecting the triploids to strong individual selection. In yet another nonlimiting embodiment, de novo tetraploids are produced by mating selected triploids and selected diploids followed by polar body I inhibition and subjecting the produced tetraploids to strong individual selection. In this nonlimiting embodiment, the de novo tetraploids can be crossed with mated tetraploids to produce improved tetraploids that contain increased genetic diversity and favorable genes selected from the diploid, triploid and tetraploid phases. Tetraploid molluscan shellfish are improved through CIB. After the production of the first-generation tetraploids, tetraploids are mated with tetraploids to produce the next generation of mated tetraploids. At the same time, tetraploids are crossed with newly improved diploids in rotation to produce mated triploids. A nonlimiting exemplary diagram of the CIB process is depicted in FIG. 2. In this process, both tetraploids and triploids are subjected to strong individual selection by selecting, for example, the top 10% performers. Eggs from the best-performing triploid females are mated with selected males from another diploid line for de novo production of tetraploids by inhibiting the release of polar body I. The de novo tetraploids are selected and crossed with mated tetraploids, completing a CIB cycle of integrating selection from diploid, triploid and tetraploid phases. The cycle is repeated using diploids from different core lines in rotation. In each breeding cycle, two sets of new genes are introduced to de novo tetraploids through a triploid phase, where selection brings genes supporting superior triploids into tetraploids. All crosses are made with at least 25 females and 25 males. While the production of mated and de novo tetraploids are known, no systematic coalescence of interploidy breeding of shellfish has been reported. By using the CIB method in accordance with the present invention, selection at different ploidy levels can be systematically integrated and favorable genes from each ploidy level are brought into tetraploids through selection and coalescence. CIB solves the problem that triploids, the cultured stock, cannot be directly improved since triploids are mostly sterile. CIB utilizes the best-performing triploids to produce tetraploids that in turn produce improved triploids. Tetraploids are also improved through 4N×4N crosses so that genes desirable for tetraploids are also selected or enriched.

The present invention also provides methods for producing improved triploid mollusks. Triploids are produced by 2N×4N crosses. Improved triploids in accordance with the present invention can be produced via crossing of any tetraploid mollusk with a diploid mollusk produced in accordance with progressive rotational crossbreeding as disclosed herein. Improved triploid mollusks can also be produced in accordance with the present invention via crossing of any diploid mollusk with a tetraploid mollusk produced in accordance with coalesced interploidy breeding as disclosed herein. Further, improved triploid mollusks can be produced in accordance with the present invention via crossing of a diploid mollusk produced in accordance with progressive rotational crossbreeding as disclosed herein and a tetraploid mollusk produced in accordance with coalesced interploidy breeding as disclosed herein.

As demonstrated herein, diploid, triploid and tetraploid forms of molluscan shellfish produced in accordance with the PRC and/or CIB methods disclosed herein exhibit significant improvement in performance in aquaculture production.

For purposes of the present invention, by "improved performance in aquaculture production" it is meant that the molluscan shellfish produced in accordance with the methods disclosed herein exhibit one or more of faster growth and/or increased effective yield and/or increased length, width, height and/or weight, and/or greater resistance as determined by higher survival to diseases as compared to molluscan shellfish not prepared by the methods disclosed herein. For purposes of the present invention, by "strong individual selection" it is meant that the top percentage of performers as molluscan shellfish are selected. In one nonlimiting embodiment, the top 10% performers are selected. For purposes of the present invention, top performance is generally measured by one or more of faster growth and/or increased effective yield and/or increased length, width, height and/or weight, and/or higher survival to diseases as compared to other molluscan shellfish of the same species.

For purposes of the present invention, by "favorable genes" it is meant genes which produce molluscan shellfish exhibiting one or more of faster growth and/or increased effective yield and/or increased length, width, height and/or weight and/or greater resistance as determined by higher survival to diseases as compared to other molluscan shellfish of the same species.

The following nonlimiting examples are provided to further illustrate the present invention. These examples are illustrative only and are not intended to limit the scope of the invention in any way.

EXAMPLES

Example 1

Improved Diploid Eastern Oysters Produced by Progressive Rotational Crossbreeding Improved diploid eastern oysters were produced using the method of PRC as depicted in FIG. 1. Three independent core lines, NEF, NEG and NEH, were established through progressive selection starting with wild oysters from Long Island Sound (LIS). All lines were selected for fast growth and higher survival under two diseases, MSX and Dermo.

NEH is an existing line from long-term selective breeding with new genetic material from LIS incorporated through a bridging line (Ford and Haskin Journal of Parasitology 1987 73:268-376; Guo et al. J. Shellfish Res. 2003 22(1):333-334). NEF were established in 2001 with about 12.5% new genetic material from Maine added through a bridging line. NEG were established in 2004 with about 12.5% genetic material from Louisiana added through a bridging line. The bridging lines were established by progressive crossing and backcrossing between the core lines and source populations following steps described above. The bridging lines were subjected to strong selection and brought into the core lines when their performance was comparable to that of the core lines.

For each cross, about 50 oysters (25 males and 25 females), representing the largest 10% of the cohort, were used as parents to produce the next generation by factorial crossing. Eggs from the females were pooled and then divided into equal aliquots, each fertilized with a male in separate beakers. Thirty minutes after fertilization, fertilized eggs were pooled and incubated in duplicate 200-1 tanks at 50 eggs/ml. At 48 hours post-fertilization, D-stage larvae were collected, counted and cultured in 200-1 tanks at a density of 10 larvae/ml. Larvae were cultured and single oyster spat were produced with standard hatchery protocols (Guo et al. Aquaculture 1996 142:149-161). Single spat from each line were deployed in three or four replicate bags for field evaluation.

A rotational cross was made by mating the production line NEX with NEH. At 18 months of age, oysters from the new production line were significantly ($p<0.01$, t-test) larger than that from the three core lines and wild controls. There was no significant difference in survival between the production line and the core lines at 18 months of age. The effective yield (average body weight×survival) of the production line is 17-42% higher than the core lines and 121% higher than the wild control thus demonstrating improvement in the production line NEX produced by PRC of the present invention.

Body size, survival and effective yield of three core lines (NEF, NEG and NEH) and the production line NEX produced by progressive'rotational crossbreeding at 18 months of age, with unselected wild oysters as control are depicted in Table 1. Numbers in parenthesis are standard error of the mean.

TABLE 1

| Lines | n | Height (mm) | Body Weight (g) | Survival (%) | Yield (g) |
|---|---|---|---|---|---|
| NEF | 100 | 67.5 (0.8) | 38.4 (0.9) | 87.5 | 33.6 |
| NEG | 100 | 62.4 (0.8) | 34.3 (0.9) | 80.9 | 27.7 |
| NEH | 100 | 70.1 (0.9) | 36.5 (1.1) | 89.6 | 32.7 |
| Production line NEX | 98 | 73.4 (1.0) | 43.0 (1.1) | 91.5 | 39.3 |
| Wild control | 100 | 51.1 (0.6) | 23.1 (0.6) | 76.9 | 17.8 |

Example 2

Improved Tetraploid and Triploid Eastern Oysters Produced by Coalesced Interploidy Breeding The performance of tetraploid and triploid oysters was improved using CIB. The first generation of tetraploids was produced by inhibiting polar body I in 3N female×2N male crosses (Guo and Allen Mol. Mar. Biol. Biotech. 1994 3(1):42-50). Mated tetraploids were subsequently produced by 4N×4N crosses. Triploids referred to herein as 2005 were produced by mating diploid females with F2 tetraploid males, and F3 mated tetraploids were produced from 4N×4N crossing of F2 tetraploids. At 6 months of age, F3 mated tetraploids were about the same size as diploids but smaller than triploids (Table 2).

CIB was conducted in the following sequences. First, triploids were produced by crossing tetraploids with improved diploids from a different core line so that one set of new chromosomes were introduced into triploids (FIG. 2). After field exposure to diseases and mortalities, the best-performing triploids (largest 10% of survivors) were selected to produce de novo tetraploids by inhibiting polar body I in 3N female×2N male crosses. Inhibition of polar body I was achieved by treating newly fertilized eggs with cytochalasin B, 6-(dimethylamino)purine or heat shock. Concurrently, mated tetraploids were produced by 4N×4N crosses and subjected to strong selection (largest 10% among survivors). After strong selection, de novo and mated tetraploids were crossed to produce the next generation of tetraploids, completing one round of CIB (FIG. 2). Each round of CIB involved crossing with diploids from two different lines, bringing two sets of chromosomes into de novo tetraploids, which in turn brings one set of chromosomes into the tetraploid line by crossing with mated tetraploids.

After two rounds of CIB, triploids and tetraploids referred to herein as 2016 showed significant ($p<0.001$, t-test) improvement in growth or body size. At 6 months of age, the 2016 tetraploids were 250% heavier than diploids, where the 2005 tetraploid before CIB was about the same as diploids (Table 2). The 2016 triploids were 88% heavier than diploids, while the 2005 triploids were 50% heavier than diploids (Table 2). The diploid controls also exhibited significantly improvements. The 2016 triploids produced by CIB were 78% heavier than the 2015 triploids produced without CIB. This example shows that tetraploids produced by CIB are significantly improved, and triploids produced from improved tetraploids and diploids are also significantly improved.

Body size of 6-month old triploids (3N), tetraploids (4N) and diploid (2N) controls before (lines 2005) and after (lines 2016) two rounds of coalesced interplay breeding in accordance with the present invention are depicted in Table 2. Numbers in parenthesis are standard error of the mean.

TABLE 2

| Lines | n | Height (mm) | Length (mm) | Width (mm) | Weight (g) |
|---|---|---|---|---|---|
| 2005: 2N | 84 | 20.6 (0.5) | 14.5 (0.3) | 6.3 (0.1) | 1.2 (0.1) |
| 2005: 3N | 94 | 22.9 (0.5) | 15.7 (0.3) | 7.4 (0.1) | 1.8 (0.1) |
| 2005: 4N | 30 | 19.6 (0.7) | 13.7 (0.5) | 6.0 (0.2) | 1.0 (0.1) |
| 2016: 2N | 96 | 29.4 (0.9) | 20.9 (0.3) | 8.4 (0.1) | 3.2 (0.2) |
| 2016: 3N | 90 | 40.9 (0.8) | 26.9 (0.3) | 10.1 (0.1) | 6.0 (0.3) |
| 2016: 4N | 30 | 49.4 (1.0) | 33.1 (0.7) | 12.4 (0.3) | 11.2 (0.6) |

What is claimed:

1. A method for producing a triploid mollusk, said method comprising:
   (a) generating a diploid mollusk with improved performance in aquaculture production by a progressive rotational crossbreeding method comprising:
      (i) deriving multiple semi-inbred core lines of diploid mollusks that are derived from independent source populations of diploid mollusks which are progressively improved through strong individual selection;

(ii) adding new genetic material to the core line to prevent severe inbreeding or complete loss of said multiple semi-inbred core lines with a bridging line that is produced by progressive crossing and backcrossing between the core line and the source population and strong individual selection of the bridging line; and (iii) rotating the multiple semi-inbred core lines for crossing with a mollusk production line used for commercial production so that genetic diversity and heterosis in the resulting crossed line are sustained and performance in aquaculture production is improved as compared to molluscan shellfish not prepared by said diploid mollusk production method; and (b) crossing a tetraploid mollusk with the diploid mollusk generated in accordance with step (a) to produce the triploid mollusk.

2. The method of claim 1 wherein the mollusk is an oyster.

3. The method of claim 1 wherein the tetraploid mollusk is produced through a method of coalesced interploidy breeding comprising:

producing mated tetraploids by tetraploid×tetraploid crosses and subjecting the mated tetraploids to strong individual selection;

producing triploids by crossing tetraploids and diploids to bring in one new set of chromosomes into triploids and subjecting said produced triploids to strong individual selection;

producing de novo tetraploids by mating selected triploids and another diploid line followed by polar body I inhibition and subjecting the produced tetraploids to strong individual selection; and crossing the de novo tetraploids with mated tetraploids to produce tetraploids that contain increased genetic diversity and favorable genes selected from the diploid, triploid and tetraploid phases and which exhibit improved performance in aquaculture production as compared to molluscan shellfish not prepared by said tetraploid mollusk production method.

4. The method of claim 3 wherein the mollusk is an oyster.

5. A method for producing a triploid mollusk, said method (a) generating a tetraploid mollusk with improved performance in aquaculture production by a coalesced interploidy breeding method comprising:

(i) producing mated tetraploids by tetraploid×tetraploid crosses and subjecting the mated tetraploids to strong individual selection;

(ii) producing triploids by crossing tetraploids and diploids to bring in one new set of chromosomes into triploids and subjecting said produced triploids to strong individual selection;

(iii) producing de novo tetraploids by mating selected triploids and another diploid line followed by polar body I inhibition and subjecting the produced tetraploids to strong individual selection; and (iv) crossing the de novo tetraploids with mated tetraploids to produce tetraploids that contain increased genetic diversity and favorable genes selected from the diploid, triploid and tetraploid phases and so that performance in aquaculture production is improved as compared to molluscan shellfish not prepared by said tetraploid mollusk production method; and (b) crossing a diploid mollusk with the tetraploid mollusk generated in accordance with step (a) to produce the triploid mollusk.

6. The method of claim 5 wherein the mollusk is an oyster.

* * * * *